(12) United States Patent
Kreuzer et al.

(10) Patent No.: US 9,636,248 B2
(45) Date of Patent: May 2, 2017

(54) DEVICES AND METHODS FOR SUPPORTING A PATIENT'S LEGS

(75) Inventors: Stefan Kreuzer, Houston, TX (US); Joseph W. Pieczynski, II, Austin, TX (US)

(73) Assignee: Innovative Orthopedic Technologies, LLC, Houston, TX (US)

( * ) Notice: Subject to any disclaimer, the term of this patent is extended or adjusted under 35 U.S.C. 154(b) by 189 days.

(21) Appl. No.: 13/418,169

(22) Filed: Mar. 12, 2012

(65) Prior Publication Data
US 2012/0233782 A1 Sep. 20, 2012

Related U.S. Application Data

(60) Provisional application No. 61/451,985, filed on Mar. 11, 2011, provisional application No. 61/585,969, filed on Jan. 12, 2012.

(51) Int. Cl.
*A61F 5/37* (2006.01)
*A61G 13/12* (2006.01)

(52) U.S. Cl.
CPC .......... *A61F 5/3761* (2013.01); *A61G 13/125* (2013.01)

(58) Field of Classification Search
CPC .... A47C 20/02–20/023; A61G 7/065–7/0755; A61G 13/12; A61G 13/1235; A61G 13/1245; A61G 13/125; A61F 5/3761
USPC ...................................... 5/621–624, 646–651
See application file for complete search history.

(56) References Cited

U.S. PATENT DOCUMENTS

| 2,533,494 | A | * | 12/1950 | Mitchell, Jr. ................. 248/160 |
| 3,817,512 | A | | 6/1974 | Torrey |
| 4,872,656 | A | * | 10/1989 | Brendgord et al. ............. 5/601 |
| 5,369,827 | A | * | 12/1994 | Parke et al. ..................... 5/649 |
| 5,908,397 | A | | 6/1999 | Tatum et al. |
| 7,832,401 | B2 | | 11/2010 | Torrie et al. |
| 8,132,278 | B1 | * | 3/2012 | Bailey .............................. 5/648 |
| 2007/0265635 | A1 | * | 11/2007 | Torrie et al. ................. 606/105 |
| 2010/0263129 | A1 | * | 10/2010 | Aboujaoude ..................... 5/650 |
| 2012/0318278 | A1 | * | 12/2012 | Aboujaoude et al. ........ 128/845 |

FOREIGN PATENT DOCUMENTS

| WO | 2005/087116 A2 | 9/2005 |
| WO | 2009/062324 A1 | 5/2009 |
| WO | 2010/083301 A2 | 1/2010 |

OTHER PUBLICATIONS

PCT/US2012/028816 International Search Report and Written Opinion dated Sep. 25, 2012 (10 p.).
European Search Report dated Nov. 5, 2014; European Application No. 12757451.5 (5 p.).
European Search Report dated Nov. 5, 2014; European Application No. 14179577.3 (5 p.).

* cited by examiner

*Primary Examiner* — Nicholas Polito
(74) *Attorney, Agent, or Firm* — Conley Rose, P.C.

(57) ABSTRACT

A system and method for securing a patient's leg during a medical or diagnostic procedure having a rail assembly including a first rail pivotally coupled to a second rail, a slider block, a pivot arm, and a sole assembly with a boot to restrain and support the patient's foot.

23 Claims, 13 Drawing Sheets

DEVICES AND METHODS FOR SUPPORTING A PATIENT'S LEGS

CROSS-REFERENCE TO RELATED APPLICATIONS

This application claims benefit of U.S. Provisional Application Ser. No. 61/451,985 filed on Mar. 11, 2011, entitled "Devices and Methods for Supporting a Patient's Leg During Surgery" and U.S. Provisional Application Ser. No. 61/585,969 filed on Jan. 12, 2012, entitled "Devices and Methods for Positioning a Patient's Leg," the disclosures of which are incorporated herein by reference in entirety for all purposes.

STATEMENT REGARDING FEDERALLY SPONSORED RESEARCH OR DEVELOPMENT

Not applicable.

BACKGROUND

Field of the Invention

This invention relates generally devices and methods for supporting and manipulating a patient's leg and foot during surgery (e.g., hip joint surgery) or diagnostic procedure. More specifically, this invention relates to devices and methods for manipulating and applying fraction to a patient's leg during surgery or diagnostic procedure.

Background of the Invention

During surgery on a patient's leg (e.g., hip or knee surgery), certain positions and orientations of the leg may be preferred by the surgeon. For example, during one phase of hip surgery, the surgeon may want to place the patient's leg in tension (i.e., traction), whereas in another phase of hip surgery, the surgeon may want to rotate the patient's leg about a certain axis while maintaining traction. Moreover, in some cases, the surgeon may want to maintain traction or a particular rotational orientation of the patient's leg while adjusting the other.

Some conventional leg and foot supporting devices enable fraction to be applied to the patient's leg, but provide limited, if any, ability to simultaneously rotate the patient's leg about one or more axes. Other conventional leg and foot supporting devices enable rotation of the patient's leg about one or more axes, but do not provide the ability to independently control and adjust the rotation of the patient's leg about different axes. Still other conventional leg and foot supporting devices enable traction and rotation of the patient's leg about an axis simultaneously, but do not allow adjustment of one while maintaining the other.

During a surgery or diagnostic procedure on a patient's leg, the patent's opposite leg (i.e., the leg that is not being operated on or diagnosed) is typically held in place by an elongate support stand placed on the operating room floor. However, once the opposite leg is held in position by the stand, the patient is not able to be easily moved about the operating room without moving the stand along with the patient, thereby increasing the logistical complications in moving the patient's position during the procedure.

Accordingly, there remains a need in the art for devices and methods that provide a surgeon or other medical professional the flexibility to independently translate and orient a patient's legs and feet during surgery relative to multiple axes. Such devices and methods would be particularly well-received if they were configured for relatively simple use by the surgeon or other medical professional.

BRIEF DESCRIPTION OF THE DRAWINGS

For a detailed description of the preferred embodiments of the invention, reference will now be made to the accompanying drawings in which.

BRIEF SUMMARY OF THE DISCLOSURE

Figure 1:
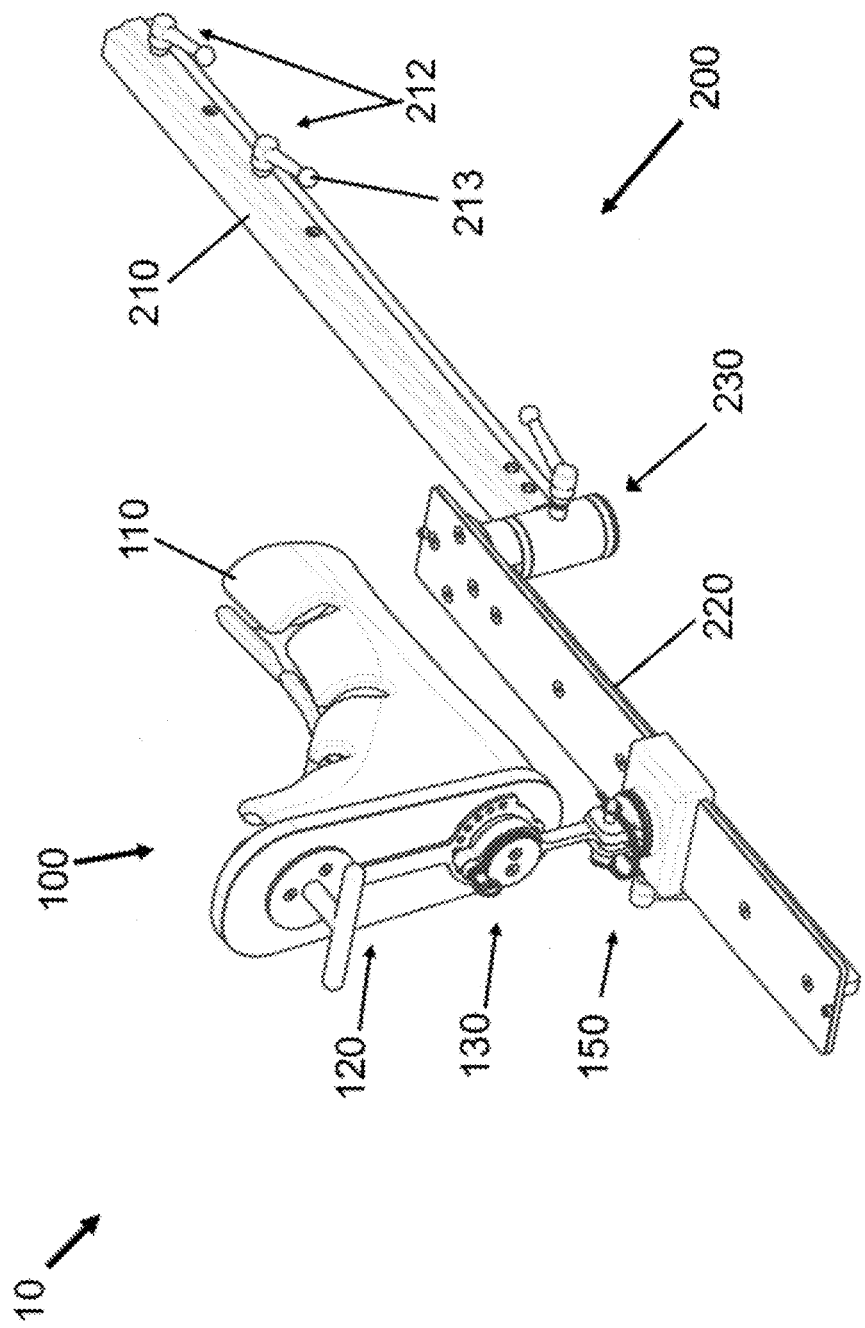
FIG. 1 is a perspective view of an embodiment of a system for manipulating the position and orientation of a patient's leg and foot in accordance with the principles described herein.

Generally, the present disclosure relates to a system comprising a rail assembly having a first rail pivotally coupled to a second rail, each rail having a longitudinal axis; a slider block slidably mounted to the second rail; a pivot arm pivotally coupled to the slider block; a sole assembly rotatably coupled to the pivot arm; and a boot mounted to the sole assembly in order to facilitate securing and repositioning a patient's leg.

Also the present disclosure relates to a device for supporting a leg of a patient, comprising: a first rail having a longitudinal axis, a first end, and a second end opposite the first end; a second rail having a longitudinal axis, a first end, and a second end opposite the first end; a pivot joint rotatably coupling the second end of the first rail to the first end of the second rail; a slider block moveably mounted to the second rail; and a foot holder configured to hold a foot of the patient coupled to the slider block.

Further, the disclosure relates to a foot holding assembly for securing a foot of a patient during a surgical or diagnostic procedure, the assembly comprising: a boot configured to hold the foot of the patient; a rigid sole coupled to the boot; and a pivot arm having a first end and a second end rotatably coupled to the sole.

Embodiments described herein comprise a combination of features and advantages intended to address various shortcomings associated with certain prior devices, systems, and methods. The various characteristics described above, as well as other features, will be readily apparent to those skilled in the art upon reading the following detailed description, and by referring to the accompanying drawings.

DETAILED DESCRIPTION OF THE PREFERRED EMBODIMENTS

The following discussion is directed to various exemplary embodiments. However, one skilled in the art will understand that the examples disclosed herein have broad application, and that the discussion of any embodiment is meant only to be exemplary of that embodiment, and not intended to suggest that the scope of the disclosure, including the claims, is limited to that embodiment.

Certain terms are used throughout the following description and claims to refer to particular features or components. As one skilled in the art will appreciate, different persons may refer to the same feature or component by different names. This document does not intend to distinguish between components or features that differ in name but not function. The drawing figures are not necessarily to scale. Certain features and components herein may be shown exaggerated in scale or in somewhat schematic form and some details of conventional elements may not be shown in interest of clarity and conciseness.

In the following discussion and in the claims, the terms "including" and "comprising" are used in an open-ended fashion, and thus should be interpreted to mean "including, but not limited to." Also, the term "couple" or "couples" is intended to mean either an indirect or direct connection. Thus, if a first device couples to a second device, that connection may be through a direct connection, or through an indirect connection via other devices, components, and connections. In addition, as used herein, the terms "axial" and "axially" generally mean along or parallel to a central axis (e.g., central axis of a body or a port), while the terms "radial" and "radially" generally mean perpendicular to the central axis. For instance, an axial distance refers to a distance measured along or parallel to the central axis, and a radial distance means a distance measured perpendicular to the central axis. Additionally, the terms "bed" and "table" as used herein refer to a patient's bed, operating table, examination bed, or any other bed used for medical procedures, operations, care, diagnostics, or combinations thereof.

Referring now to FIG. 1, an embodiment of a system 10 for manipulating the position and orientation of a patient's leg during a surgical or diagnostic procedure is shown. For example, system 10 may be used to support and manipulate the patient's leg undergoing the procedure, referred to herein as the "affected" leg, or the patient's opposite leg (i.e., the patient's leg that is not the subject of the procedure), referred to herein as the "unaffected" leg. In this embodiment, system 10 includes a foot holding device or assembly 100 moveably coupled to a rail assembly 200. In general, a patient's foot is secured to foot holding assembly 100 and supported by rail assembly 200. Together, foot holding assembly 100 and rail assembly 200 are used to manipulate the patient's foot and ankle to vary the position and orientation of the patent's corresponding leg (affected or unaffected leg), as well as controllably apply fraction to the patient's corresponding leg.

In general, the components of system 10 may be constructed of any suitable material(s), but are preferably constructed of material(s) that can be sterilized, for example by an autoclave. Suitable materials include, without limitation, composites, plastics, metals and metal alloys, or combinations thereof. As will be described in more detail below, system 10 is modular, such that any of the components of system 10 can be sterilized independent of the other components in cases where select components are exposed during the procedure (i.e., not covered by sterile drapes) whereas other components are not exposed during the procedure (i.e., covered by sterile drapes). In addition, the modularity of system 10 enables replacement of worn or damaged parts without having to replace the entirety of system 10.

Figure 2:
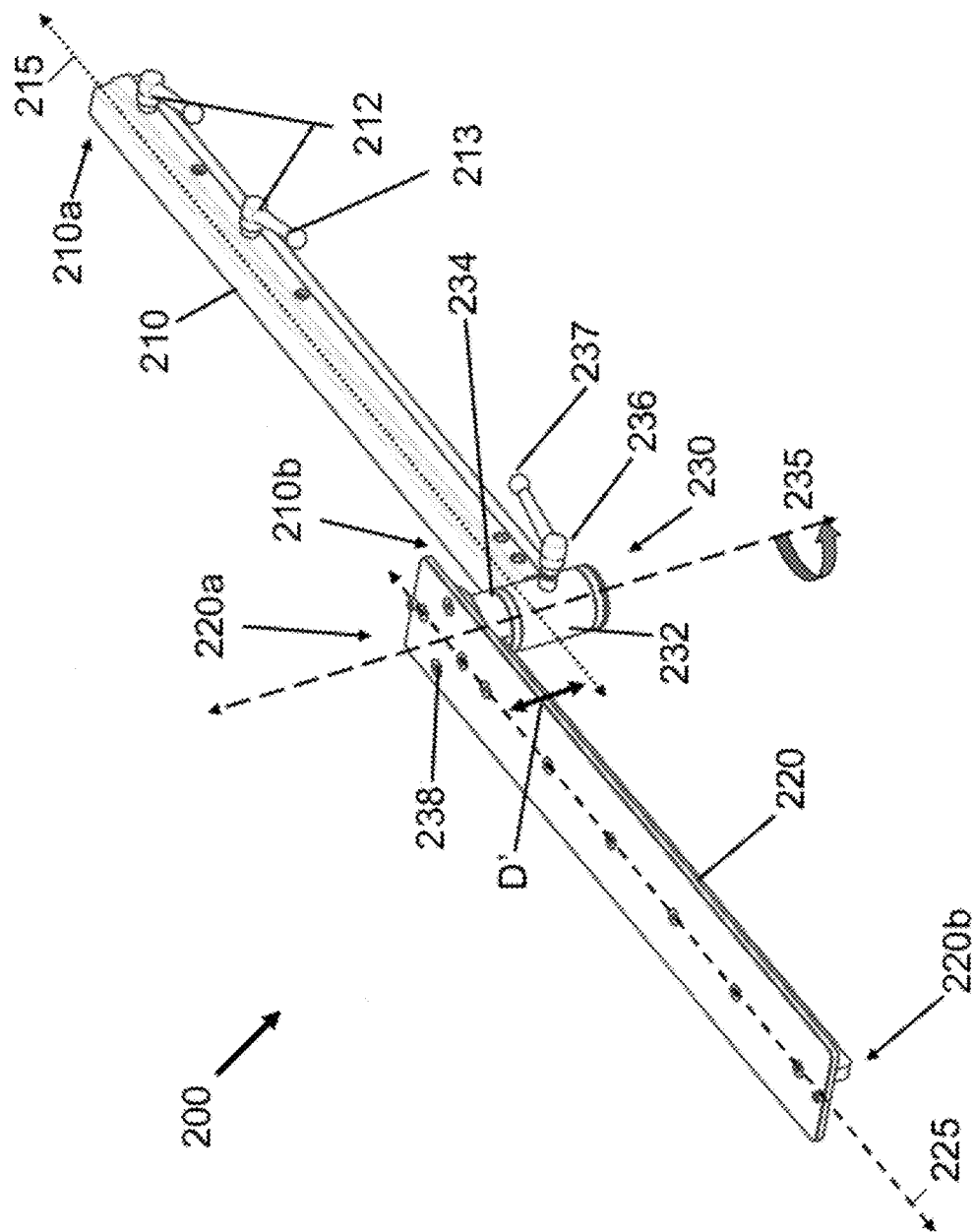
FIG. 2 is a perspective view of the rail assembly of FIG. 1.

Referring now to FIGS. 1 and 2, rail assembly 200 includes an elongate rigid first rail 210 and an elongate rigid second rail 220 pivotally coupled to first rail 210. In particular, second rail 220 is coupled end-to-end to first rail 210 with a hinge or pivot joint 230 that allows second rail 220 to rotate relative to first rail 210 about a vertical axis of rotation 235.

Figure 3:
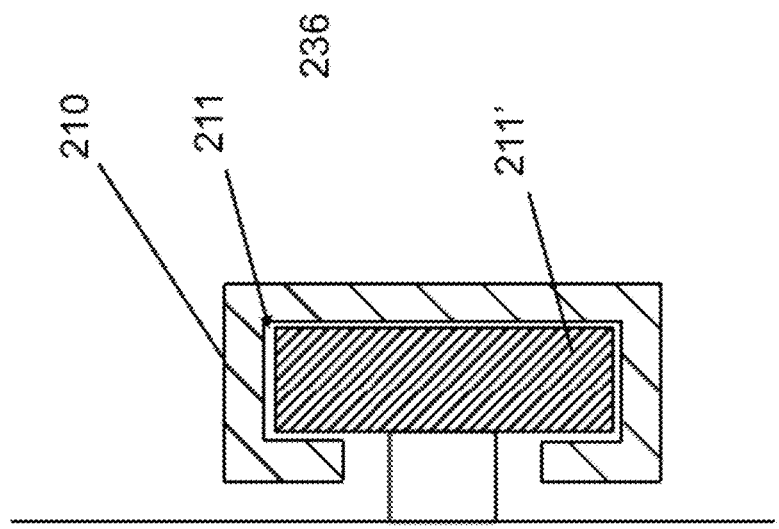
FIG. 3 is a cross-sectional view of the first rail of FIG. 1 mounted to a mating rail on the side of a bed.
Figure 4:
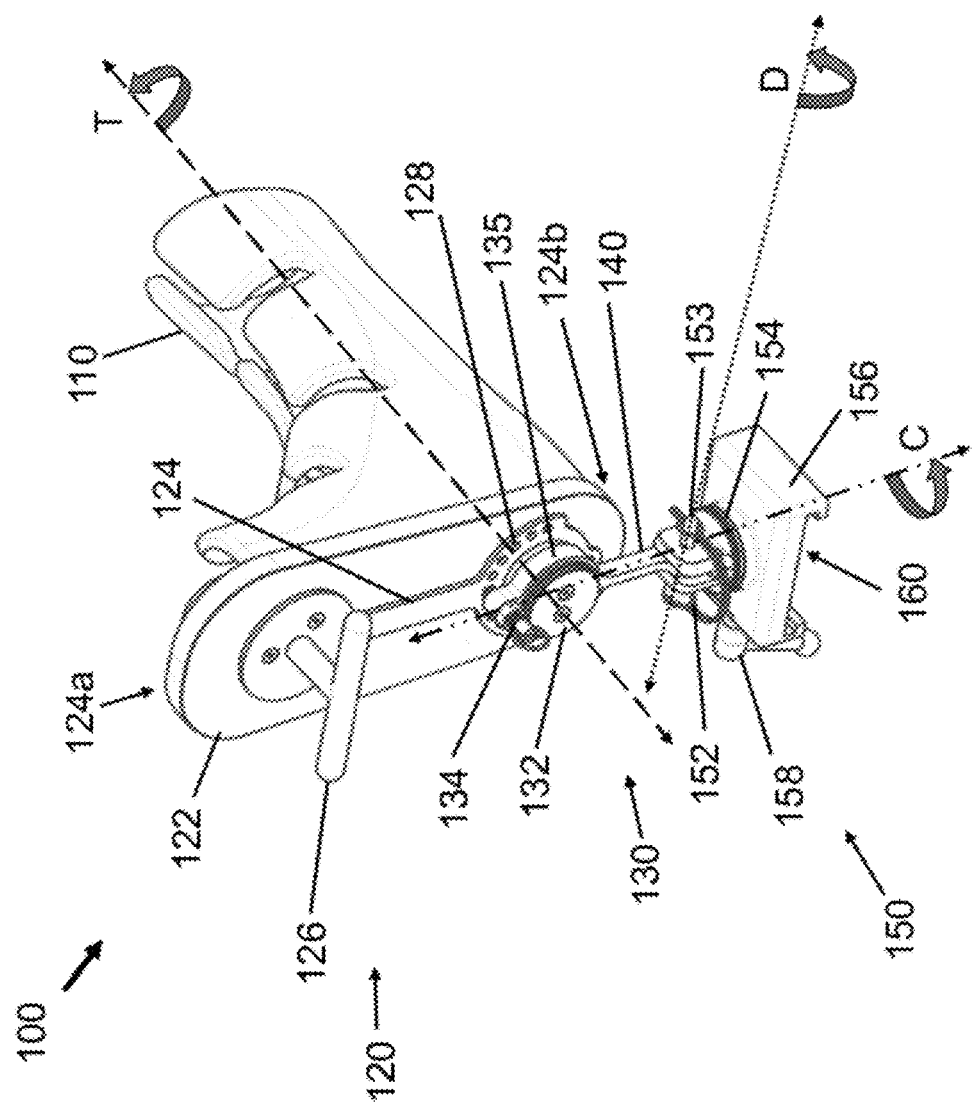
FIG. 4 is an enlarged perspective view of the foot holder device of FIG. 1.
Figure 5:
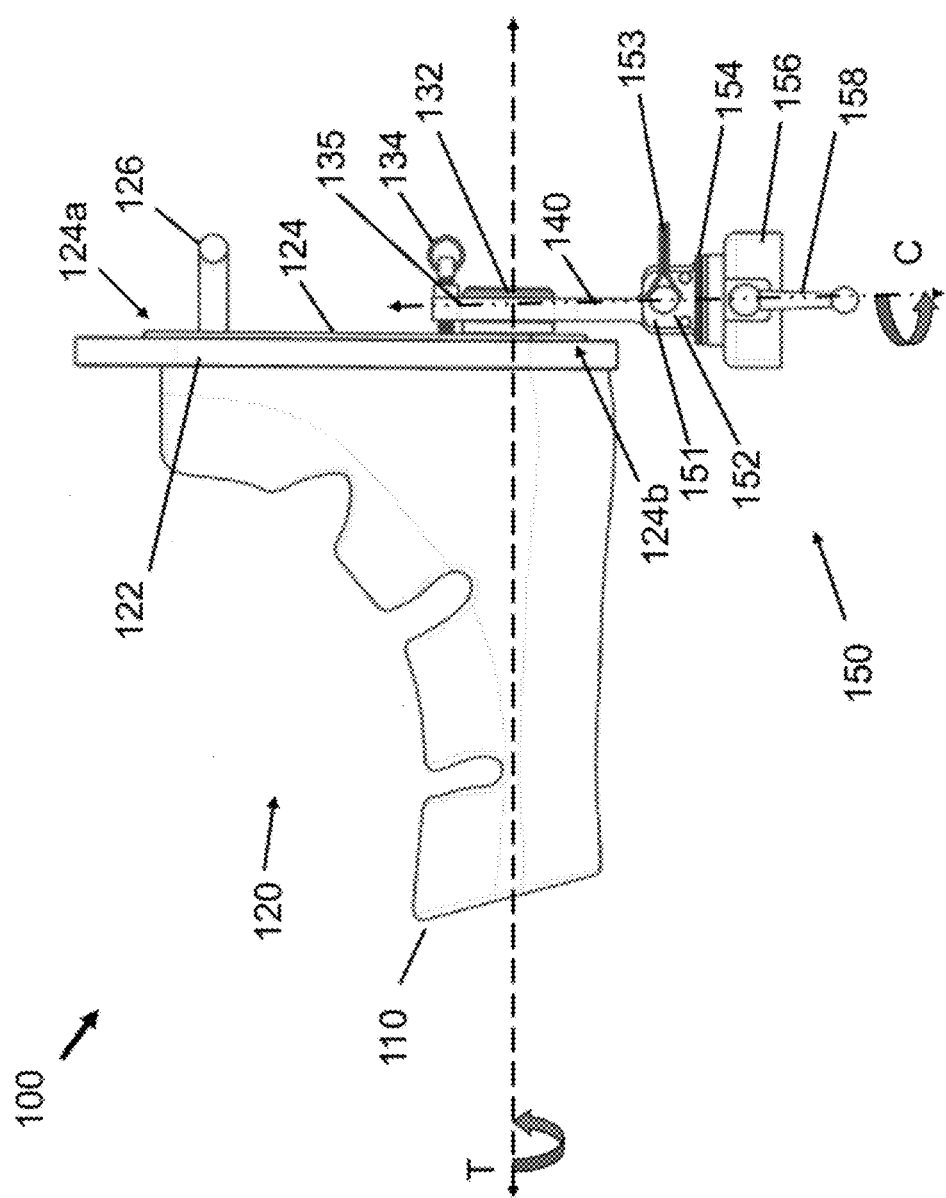
FIG. 5 is a side view of the foot holder device of FIG. 1.
Figure 6:
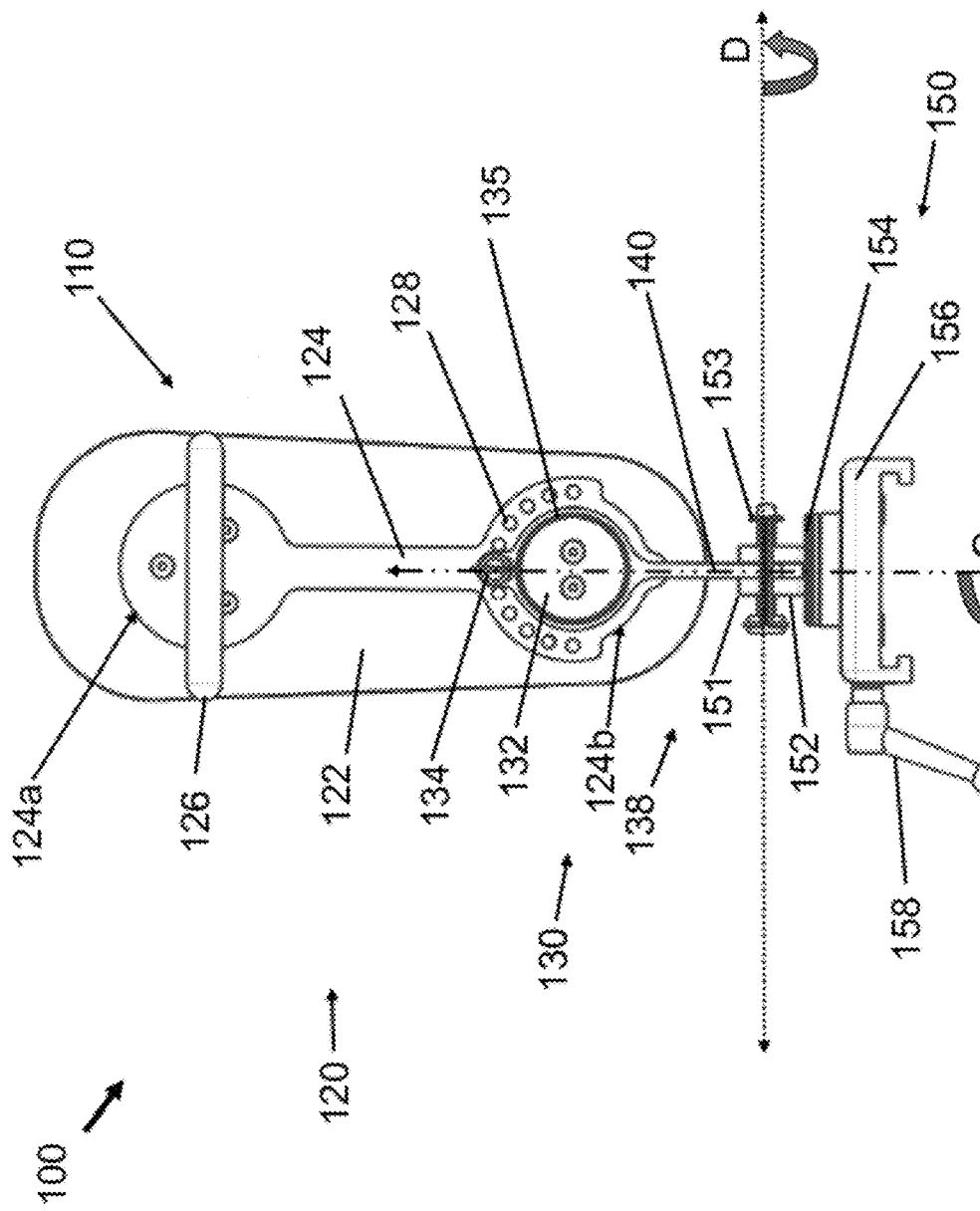
FIG. 6 is a rear view of the foot holder device of FIG. 1.

First rail 210 has a central or longitudinal axis 215, a first end 210a, and a second end 210b opposite first end 210a. In addition, first rail 210 is configured to reversibly and adjustably attach system 10 to a diagnostic or operating bed, with the remainder of system 10 cantilevered from first rail 210 and the bed. As best shown in FIG. 3, first rail 210 includes a C-channel or recess 211 extending axially from end 210a and configured to slidably receive a mating rail 211' extending from the side of the bed. The symmetric C-channel recess 211 allows first rail 210 to be coupled to a mating rail on either side of the bed—both sides of the bed include identical rails 211', and thus, first rail 210 can simply be flipped over to align and slidingly engage C-channel 211 with the rail 211' on either side of the bed. In addition, since first rail 210 slidingly engages a mating bed rail 211', first rail 210 may be moved axially relative to the bed rail 211' to position first rail 210 at any desired axial position relative to rail 211' and the bed.

Referring again to FIGS. 1 and 2, first rail 210 includes a pair of quick release connectors 212 configured to releasably lock first rail 210 to mating rail 211', thereby allowing the surgeon or medical professional to lock and secure first rail 210 to rail 211' at the desired axial position. In this embodiment, each quick release connector 212 comprises threaded member or shaft that is threadingly advanced into and out of engagement with rail 211' disposed within recess 211. Each connector 212 includes a handle 213 coupled to the threaded member that enables rotation and threaded advancement and withdrawal of the threaded member relative to the rail 211'. Thus, the threaded member of each connector 212 has a locked position advanced into fixed engagement with the corresponding rail 211' and an unlocked position withdrawn and slidably engaging the corresponding rail 211'. Consequently, when one or both quick release connectors 212 are locked, first rail 210 is restricted and/or prevented from being moved translationally or rotationally relative to the corresponding rail 211' and bed. However, when both quick release connectors 212 are unlocked, first rail 210, and hence system 10, can be moved axially relative to the corresponding rail 211' and bed, thereby enabling first rail 210 and system 10 to be axially extended from the table to varying degrees as desired by the surgeon or medical practitioner.

Referring still to FIGS. 1 and 2, second rail 220 supports foot holding assembly 100 and has a central or longitudinal axis 225, a first end 220a, and a second end 220b opposite first end 220a. First end 220a is rotatably coupled to second end 210b of first rail 210 with pivot joint 230. Further, axis 225 lies in a horizontal plane spaced above a horizontal plane containing axis 215 by a vertical distance D'. Thus, second rail 220 may pass over first rail 210 as it is rotated about pivot joint 230 in arc W (shown in FIG. 12). In this embodiment, second rail 220 has a general "T" shaped cross-sectional shape, however, in general, the second rail (e.g., rail 220) may have any suitable cross-sectional shape (e.g., "I" shaped).

Pivot joint 230 pivotally couples ends 210b, 220a of rails 210, 220, respectively, and allows second rail 220 to rotate about vertical axis 235 relative to first rail 210. A projection of axis 225 of second rail 220 intersects and is oriented perpendicular to axis 235. Thus, end 220b circumscribes a circular arc disposed at a fixed radius from axis 235. In this embodiment, pivot joint 230 comprises a tubular housing 232 and a cylindrical element 234 concentrically disposed within and slidably engaging housing 232. Thus, element 234 has an outer diameter that is substantially the same or slightly less than the inner diameter of housing 232. Housing 232 is attached to end 210b of first rail 210 and element 234 is coupled to end 220a of second rail 220 with a coupling member or mount 238. Element 234 may be coaxially inserted into either axial end of housing 232, thereby enabling second rail 220 to be rotatably coupled to first rail 210 regardless of the side of the bed to which first rail 210 is attached. In other words, if first rail 210 is inverted as it is switched from one side of the bed to the other, element 234 may simply be inserted into the opposite end of housing 232 to position second rail 220 above first rail 210 while allowing second rail 220 to rotate relative to first housing about axis 235. In alternative configurations, pivot joint 230 may be configured as any pivotable joint, for example a hinge, a ball-in-socket, a bushing or bearing and shaft configuration, or a universal joint, without limitation.

Pivot joint 230 also includes a pivot lock 236 to releasably lock element 234 relative to housing 232, thereby locking the angular position of second rail 220 relative to first rail 210. In this embodiment, pivot lock 236 comprises a threaded member or shaft that extends radially through housing 232 and is threadingly advanced into and out of engagement with element 234. Lock 236 includes a handle 237 coupled to the threaded member that enables rotation and threaded advancement and withdrawal of the threaded member relative to housing 232. Thus, the threaded member of lock 236 has a locked position radially advanced into fixed engagement with element 234 and an unlocked position radially withdrawn and slidably engaging the element 234. Consequently, when lock 236 is locked, element 234 is restricted and/or prevented from rotating relative to housing 232 about axis 235, thereby restricting and/or preventing second rail 220 from rotating relative to first rail 210. However, when lock 236 is unlocked, element 234 is free to rotate relative to housing 232, thereby enabling second rail 220 to be rotated relative to first rail 210 to varying degrees as desired by the surgeon or medical professional. In some embodiments, pivot joint 230 may be configured to allow adjustment of the vertical distance D'. For example, pivot lock 236 may be configured to support a vertical displacement of pivot joint 230 relative to the first rail 210 to along axis 235.

Referring now to FIGS. 4-9, foot assembly 100 is moveably coupled to second rail 220 and comprises a boot 110, a sole assembly 120, a rotatable coupling 130, a pivot arm 140, and a slider block 150. Boot 110 is attached to sole assembly 120 and is shaped and sized to receive and secure the patient's foot to foot assembly 100. Rotatable coupling 130 rotatably and adjustably couples sole assembly 120 to pivot arm 140. Slider block 150 is pivotally and adjustably coupled to coupling 130 with pivot arm 140. In addition, slider block 150 is slidably mounted to second rail 220 and allows the axial position of foot assembly 100 on second rail 220 to be controllably adjusted.

Referring still to FIGS. 4-9, slider block 150 comprises a retainer 152, an annular bearing 154, a base or body 156, and a stop release 158. Body 156 is slidably mounted to second rail 220 and may be moved axially along second rail 220 between ends 220a, b. In this embodiment, body 156 includes a C-channel or recess 160 in its lower surface that slidably receives second rail 220. Thus, body 156 may be moved axially along rail 220, but is prevented from moving laterally or rotating relative to rail 220. Body 156 may include bushings, bearings, rollers or sliding surfaces to facilitate the smooth movement of body 156 along rail 220. For example, pads 161 are disposed with recess 160 to facilitate slidable translation. Pads 161 are configured as non-metallic or semi-metallic anti-friction material.

Bearing 154 is disposed in an annular throughbore in the upper side of block 156 and supports retainer 152. Bearing 154 allows retainer 152 to rotate about a vertical axis C relative to body 156. A projection of axis C is perpendicular to and intersects axis 225 of rail 220. Bearing 154 may be a bearing, a bushing, an axle, or any device configured to permit rotation about axis C.

Figure 9:
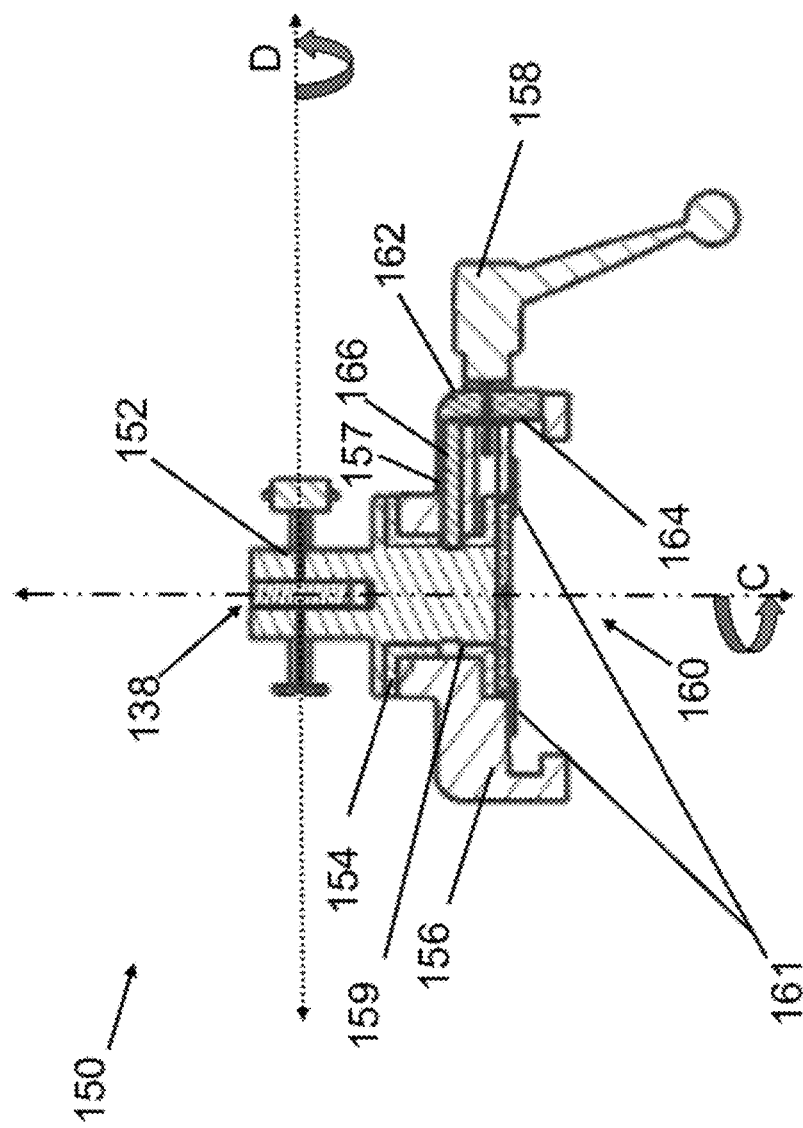
FIG. 9 is a cross-sectional front view the locking block of the foot holder device of FIG. 1.

As best shown in FIG. 9, a stop release 158 allows the surgeon or medical professional to lock the axial position of body 156, and hence slider block 150, along second rail 220. In this embodiment, stop release 158 comprise threaded member or shaft that urges a block 162 radially (relative to axis C) into and out of fixed engagement with rail 220 disposed within recess 160. Block 162 forms a portion of the inner wall 164 of body 156 defining recess 160, and can be moved by into and out of engagement with second rail 220 with stop release 158. In particular, stop release 158 has a locked position urging block 162 radially inward (relative to axis C) into fixed engagement with rail 220 and an unlocked position allowing block 162 to move slightly radially outward (relative to axis C) into sliding engagement with rail 220. Thus, when stop release 158 is locked, slider block 150 is restricted and/or prevented from being moved axially along rail 220. However, when stop release 158 is unlocked, slider block 150 may be moved axially along rail 220, thereby enabling the adjustment of the axial position of slider block 150 and foot assembly 100 along rail 220 as desired by the surgeon or medical professional.

In this embodiment, stop release 158 may also be employed to releasably lock retainer 152 relative to body 156. In particular, body 156 includes a through bore 157 extending radially (relative to axis C) from block 162 to an annular slot 159 in bearing 154. A rigid pin 166 is slidingly disposed in the through bore 157 and extends through slot 159. Pin 166 has one end engaging block 162 and the opposite end radially adjacent retainer 152. In addition, pin 166 is sized (e.g., has a length) such that when stop release 158 is in the locked position, block 162 urges pin 166 into fixed engagement with retainer 152, thereby restricting and/or preventing retainer 152 from rotating relative to body 156 about axis C. However, when block 162 is in the unlocked position, pin 166 is in sliding engagement with retainer 152. Thus, with pin 166 disposed in through bore 157, radially inward advancement of block 162 simultaneously locks body 156 relative to rail 220 and locks retainer 152 relative to block 156. However, if pin 166 is removed from bore 157, then radial advancement of block 162 locks body relative to rail 220, but does not simultaneously lock retainer 152 relative to block 156. In some embodiments, a plurality of pins 166, each disposed in a corresponding through bore 157 in body 156, are employed such that the retainer 152 is held by at least two-points of contact.

Figure 13:
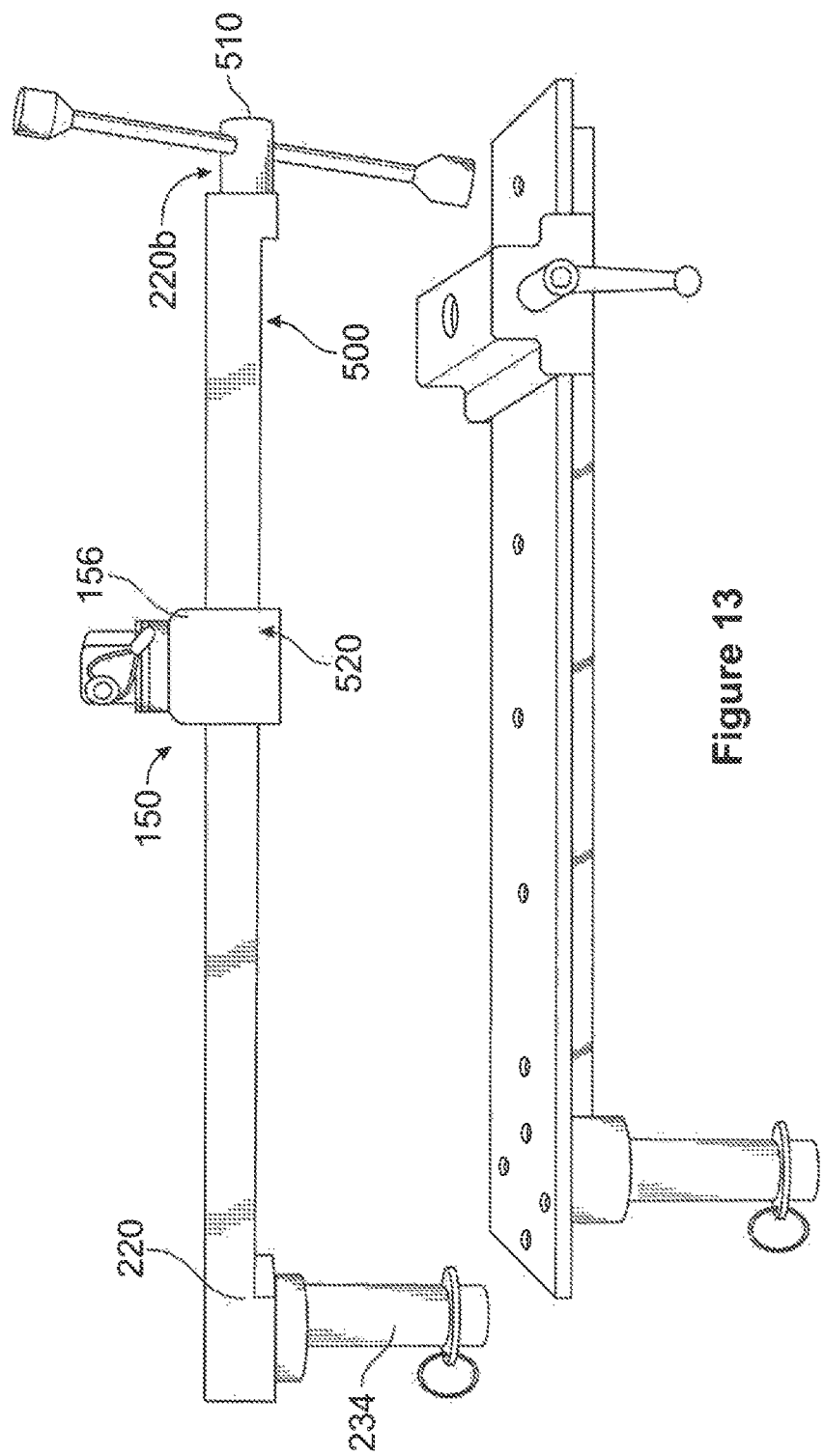
FIG. 13 is a perspective photograph of an embodiment of a rail including an actuator for controllably moving the boot assembly of FIG. 1.

In the embodiment shown in FIGS. 1 and 2, slider block 150 is manually moved along second rail 220 and locked in the desired axial position along rail 220. However, in other embodiments, the slider block may be controllably moved along the second rail by an actuator. For example, referring now to FIG. 13, slider block 150 is controllably moved axially along rail 220 by an actuator 500. In this embodiment, actuator 500 comprises a control 510 positioned at the second end 220*b* of second rail 220. Actuator 500 interfaces with a portion of body 156 with an engagement structure 520 to facilitate movement of block 150 along second rail 220. More specifically, actuator 500 is a threaded rod and engagement structure 520 is a complementary internally threaded body coupled to body 156, and control 510 is a hand crank coupled to the threaded rod. Thus, rotation of control 510 causes rotation of the threaded rod and corresponding threading and unthreading of the threaded rod from engagement structure 520, thereby moving engagement structure 520, and hence slider block 150) axially along second rail 220. Alternatively, the actuator (e.g., actuator 500) may be a hydraulic, pneumatic, or electric piston. In these embodiments, the actuator may be disposed on second rail 230 or in a recess in second rail 230. In further instances, the engagement structure (e.g., engagement structure 520) is a t-slot nut, T-slot bolt. or T-bolt, for engaging the actuator and configured for rotational or linear translation of the block 150 along the second rail 230. Additionally, in alternate configurations, the control 510 is a switch or button in electric or mechanical communication with the actuator 500 to remotely control the rotational or linear translation of the slider block 150 along the second rail 230.

Referring again to FIGS. 4-9, retainer 152 is pivotally coupled to rotatable coupling 130 with pivot arm 140. In particular, the upper end of retainer 152 includes a pair of parallel, spaced extensions arms 151. The lower end of pivot arm 140 is disposed between arms 151, and a removable pin 153 is disposed in aligned bores in arms 151 and the lower end of arm 140. Pin 153 has a horizontal central axis D about which pivot arm 140 is free to rotate. Pivot arm 140 is reversibly coupled to retainer 152 with pin 153. Thus, by removing pin 153, pivot arm 140 may be rotated 180° about axis C and recoupled to retainer 152 with pin 153.

Figure 7:
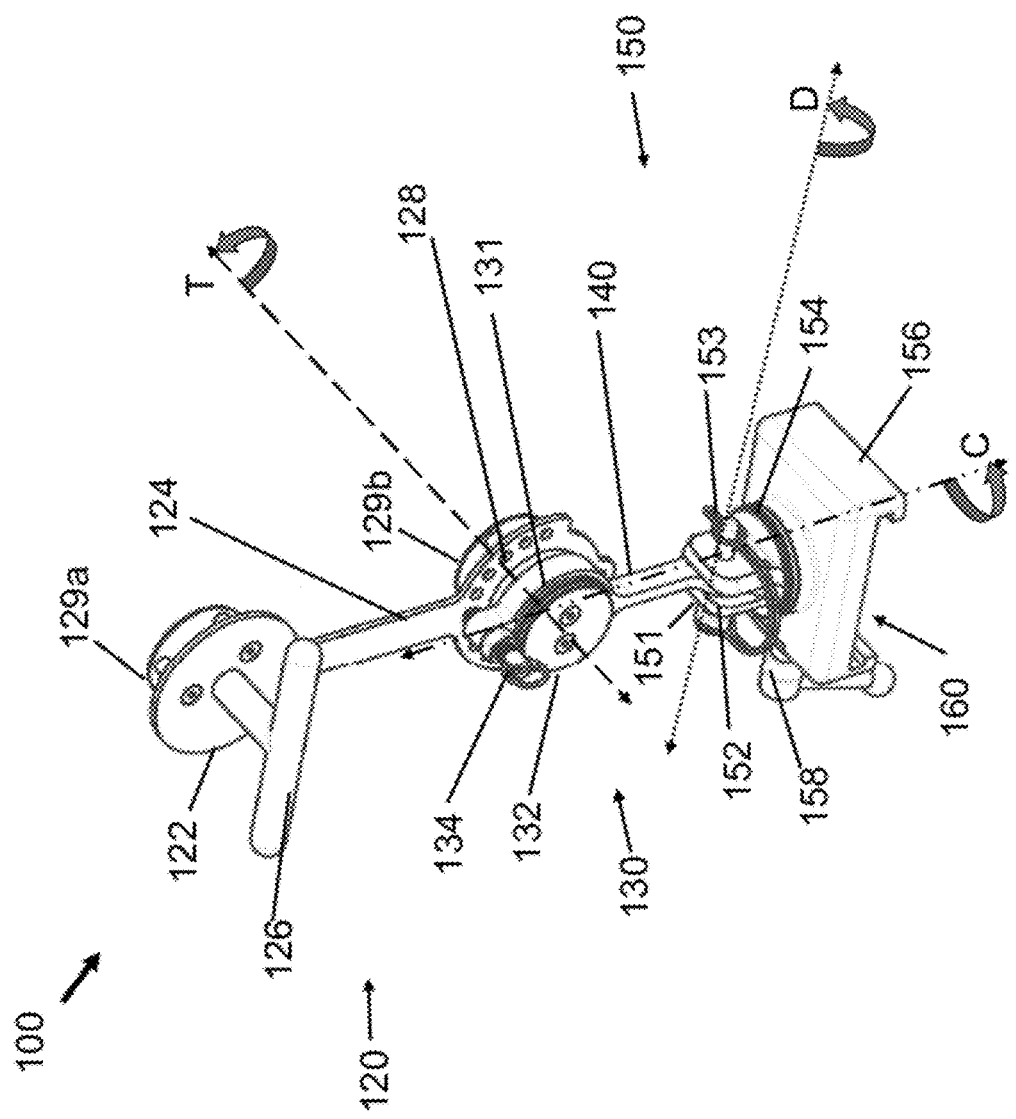
FIG. 7 is a perspective view of the foot holder device of FIG. 1 with the boot removed for clarity.
Figure 8:
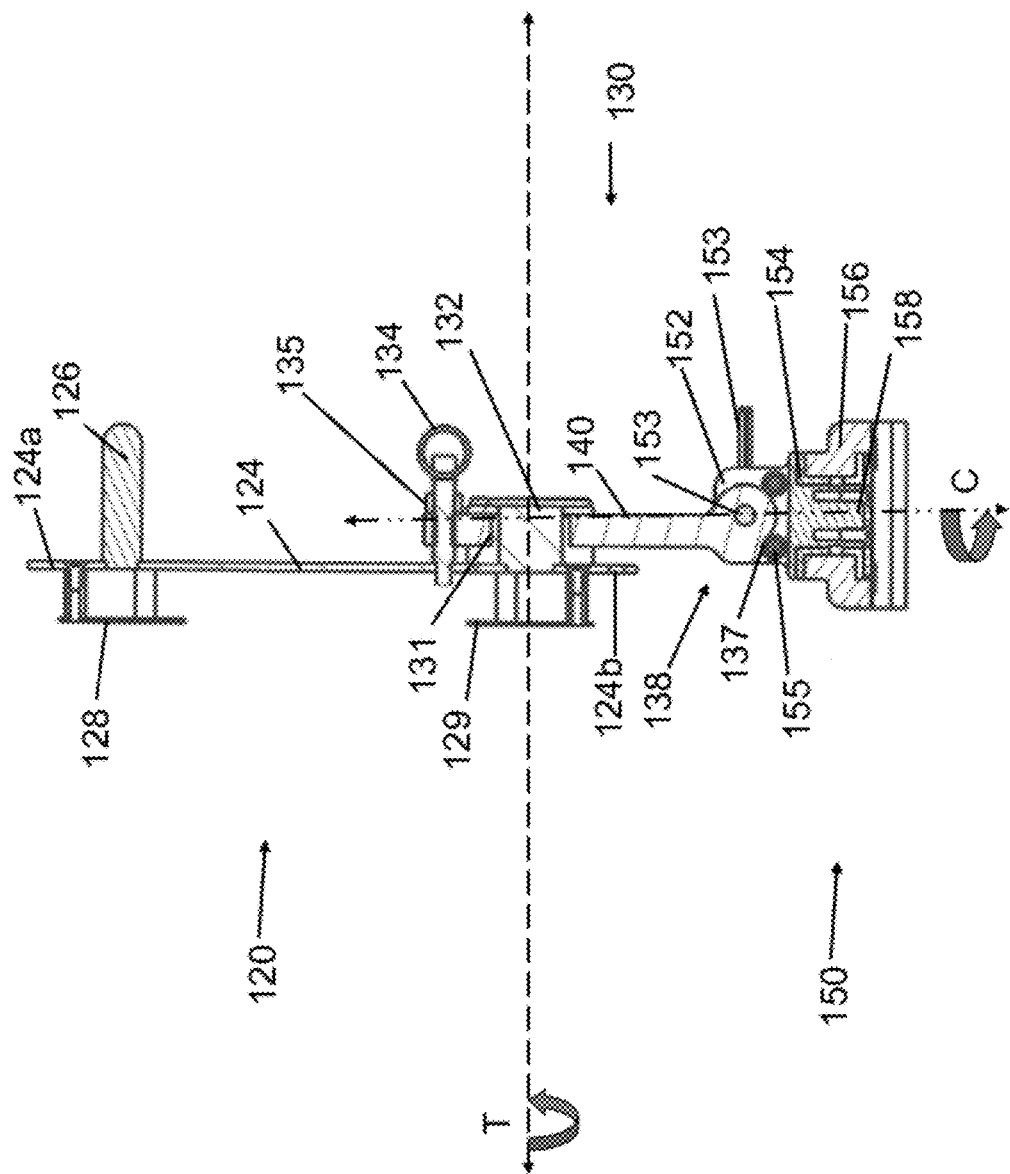
FIG. 8 is a cross-sectional side view of the foot holder device of FIG. 1 with the boot removed for clarity.

Axis D is perpendicular to and intersects vertical axis C. As best shown in FIG. 8, a pair of stops 155 extend between arms 151 parallel to pin 153, and are radially spaced from pin 153. Stops 155 limit the rotation of pivot arm 140 about axis D. Specifically, pivot arm 140 can rotate about axis D to the left in FIG. 8 until a notch 137 in lower end of pivot arm 140 engages stop 155 on the left in FIG. 8, which prevents continued rotation of pivot arm 140 about axis D in that direction; and pivot arm 140 can rotate about axis D to the right in FIG. 8 until pivot arm 140 engages stop 155 on the right, which prevents continued rotation of pivot arm 140 about axis D in that direction. It should be appreciated that stop 155 on the left in FIG. 7 is positioned to prevent pivot arm 140 from rotating from vertical to the left, thereby reducing the potential for an inadvertent hyperextension of the patient's knee. To the contrary, the stop 155 on the right in FIG. 7 is positioned to allow pivot arm 140 to rotate from vertical to the right through an angle greater than 90°. Stops 155 may be rollers configured to assist the substantially parallel alignment of the pivot arm 140 and the extension arms 151.

Referring now to FIGS. 4-8, boot 110 includes a rigid sole 122 that is mounted to sole assembly 120. Boot 110 preferably includes straps, belts, snaps or other similar devices for securing a patient's foot therein. In general, boot 110 may be sewn, molded, fused or otherwise secured to sole 122.

In this embodiment, sole assembly 120 includes a boot plate 124 having an upper end 124*a* secured to the forefoot or toe portion of sole 122 and a lower end 124*b* secured to the ankle or heel portion of sole 122. In particular, plate 124 is secured to mounts 129*a*, 129*b* embedded in sole 122. A handle 126 extends perpendicularly from upper end 124*a* of plate 124 and is used by the surgeon to manipulate the position and orientation of the patient's foot, and hence, manipulate the position and orientation of the patient's leg. Lower end 124*b* of plate 124 is generally annular and includes a plurality of circumferentially spaced detents 128, each disposed at a common radius from an axis T that is perpendicular to sole 122 and generally aligned with the patient's tibia when the patient's foot is secured within boot 110. In this embodiment, detents 128 are uniformly circumferentially spaced about axis T. Detents 128 are preferably angularly spaced about 2-5° apart relative to each other.

Referring still to FIGS. 4-8, rotatable coupling 130 includes a generally cylindrical shaft 132 rotatably disposed in a through bore 131 in the upper end of pivot arm 140 and is secured to lower end 124*b* of boot plate 124. A bearing, bushing, rollers, etc. may be positioned between shaft 132 and pivot arm 140 to facilitate the smooth rotation of shaft 132 relative to pivot arm 140. Shaft 132 has a central axis that is aligned with axis T. Thus, shaft 132 is configured to rotate sole assembly 120 about the axis T, which is generally oriented perpendicular to sole 122 and parallel to the patient's tibia when the patient's foot is secured in foot assembly 100.

A retainer 134 configured to releasably engage detents 128 extends through the upper end of pivot arm 140. When retainer 134 is seated in a detent 128, sole assembly 120 is rotationally locked relative to pivot arm 140. Thus, when retainer 134 engages a detent 128, sole assembly 120 cannot be rotated about axis T relative to pivot arm 140. In this embodiment, retainer 134 is a pin biased into engagement with plate 124. Thus, to rotate sole assembly 120 relative to pivot arm 140, retainer 134 is pulled out of engagement with one detent 128, thereby allowing the surgeon to rotate sole assembly 120 about axis T. When sole assembly 120 is in the desired rotational orientation relative to pivot arm 140, retainer 134 is released and allowed to engage a different detent 128.

In further alternate configurations, it may be envisioned that pivot arm 140 is fixably coupled to the sole assembly 120. In these embodiments, the pivot arm 140 and sole 122 may be considered co-axial or co-linear as they extend from the arms 151 of the slider block 150. In this configuration, the foot assembly 100 may not be rotated about axis T. In certain instances, this embodiment permits the positioning and partial manipulation of the patient's affected or unaffected leg in relation to axis C and axis D.

Figure 10:
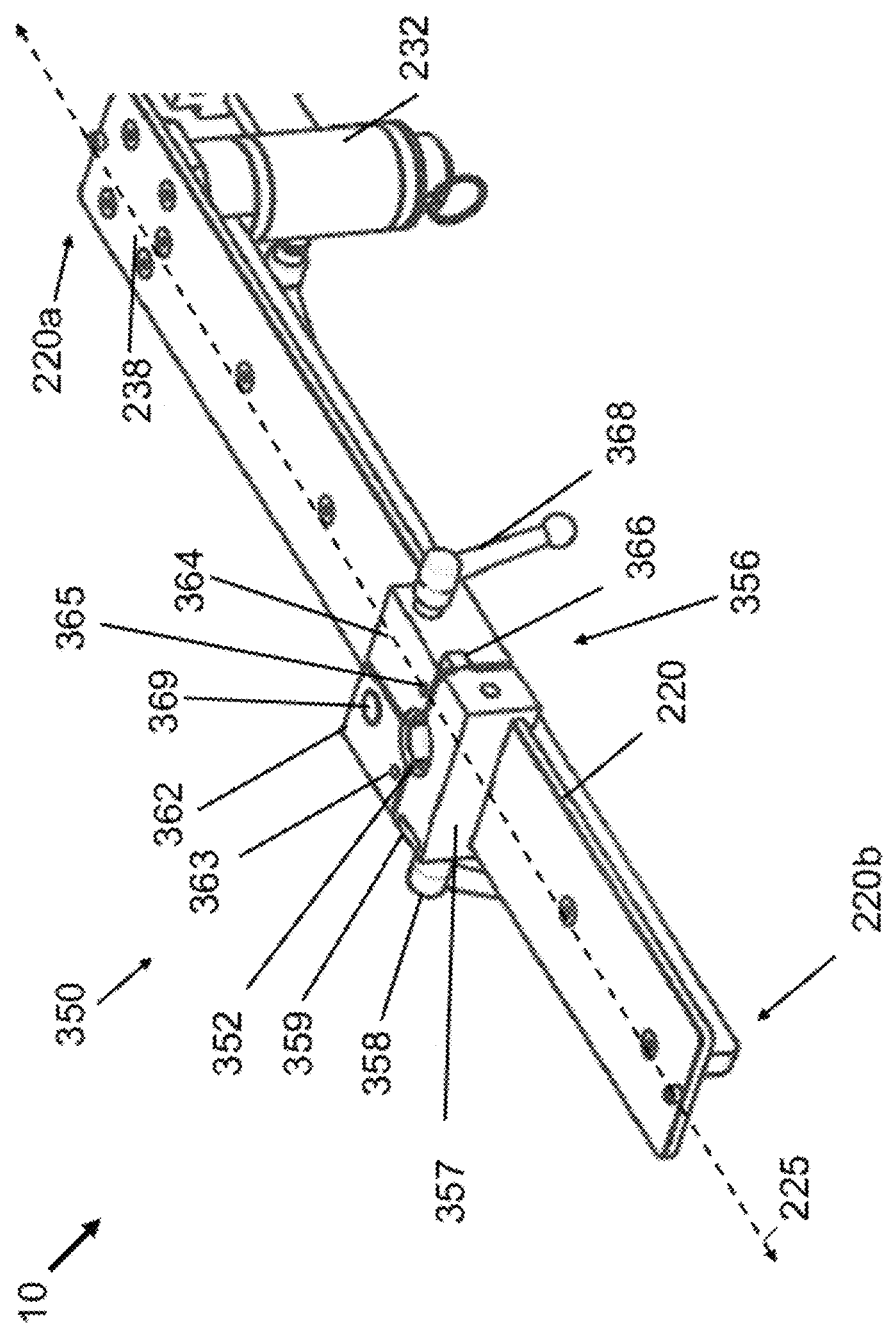
FIG. 10 is a perspective view of the rail assembly in FIG. 1 with an alternate configuration of a locking block.
Figure 11:
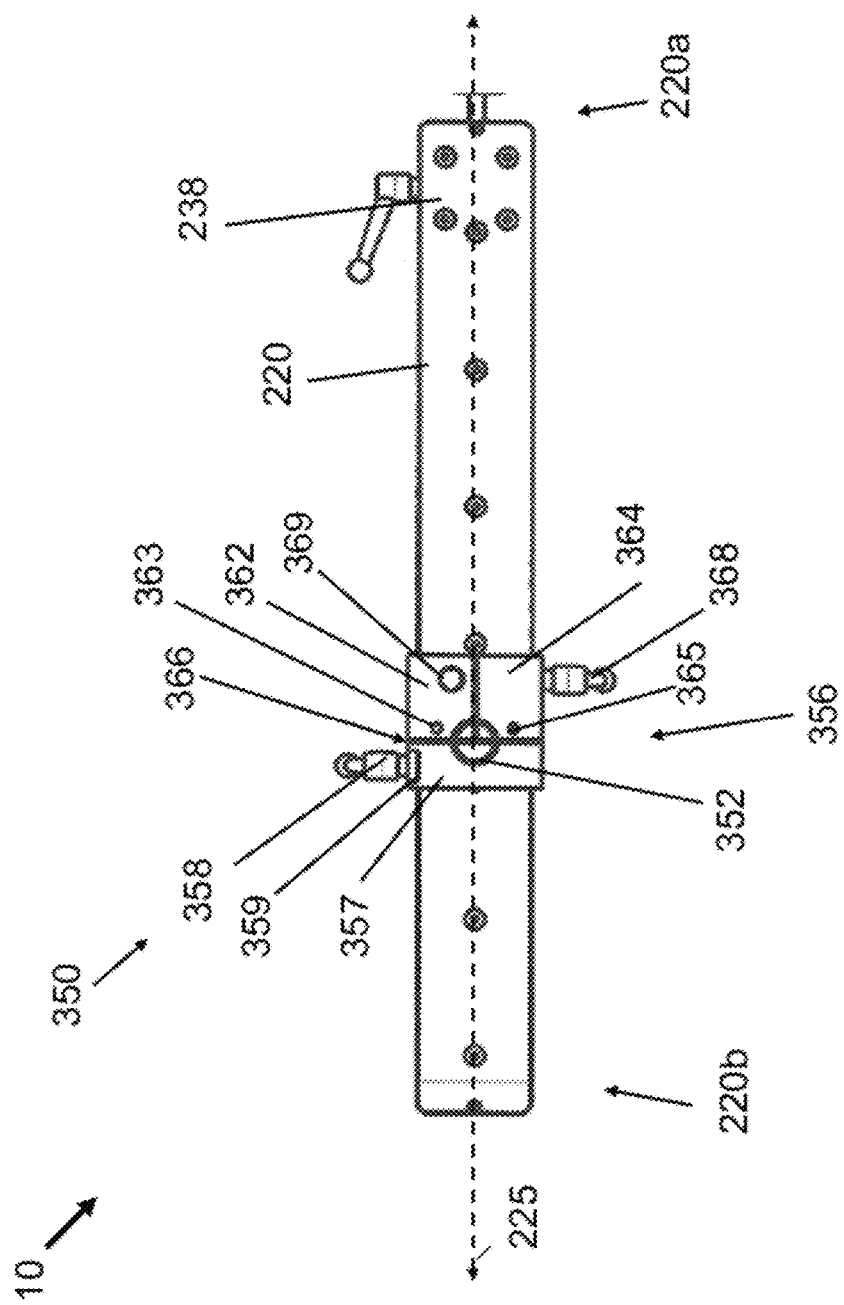
FIG. 11 is a top view of view of the rail assembly in FIG. 1 with an alternate configuration of a locking block.

Referring now to FIGS. 10 and 11, there is illustrated a system 10 comprising an alternate configuration of the slider block 350. In embodiments, the block 350 is configured to interface with any configuration of a foot assembly 100 described herein and in certain instance, with a foot assembly 100 comprising a fixably coupled pivot arm 140 and sole assembly 120. In further embodiments, pivot arm 140 may comprise a solid ball or similar radiused structure as the pivot interface 138. The slider block 350 comprises a retainer 352, a segmented base or body 356, and a stop release 158. Body 356 is slidably mounted to second rail 220 and may be moved axially along second rail 220 between ends 220a, b. In this embodiment, body 356 includes a C-channel or recess (i.e. 160 in FIG. 9) in its lower surface that slidably receives second rail 220. Thus, body 356 may be moved axially along rail 220, but is prevented from moving laterally or rotating relative to rail 220. Body 356 may include bushings, bearings, rollers or sliding surfaces to facilitate the smooth movement of body 356 along rail 220. For example, body 356 comprises pads or other anti-friction material (i.e. 161 in FIG. 9) to facilitate axial translation as described hereinabove.

In embodiments, body 256 comprises a lateral segment 357 and two complementary segments 362, 364. Disposed at the interface of a lateral segment 357 and the two complementary segments 362, 364 is a retainer 352. Retainer 352 is configured to receive and pivotably retain the interaface 138 of the pivot arm 140. Generally, complementary segments 362, 364 are configured to move relative to one another and lateral segment 357 in response to insertion of interface 138 into retainer 352. Alternatively, complementary segments 362, 364 are motivated by a resilient member or resilient interface. Longitudinal and lateral displacement of complementary segments 362, 364 from lateral segment 357 changes the configuration of retainer 352. Retainer 352 is opened when release 368 is in the open position, such that the interface 138 is pivotably retained therein.

Lateral segment 357 extends across second rail 220 perpendicular to the longitudinal axis 225. Stop release 358 is disposed on lateral segment 357 and allows the surgeon or medical professional to lock the axial position of slider block 350, along second rail 220. In this embodiment, stop release 358 comprise threaded member or shaft that urges a pressure pad 359, block, or similar structure (as described hereinabove) into and out of fixed engagement with rail 220. In particular, stop release 358 has a locked position in fixed engagement of pressure pad 359 with rail 220 and an unlocked position allowing sliding engagement with rail 220. Thus, when stop release 358 is locked, body 356 is restricted and/or prevented from being moved axially along rail 220. However, when stop release 358 is unlocked, body 356 may be moved axially along rail 220, thereby enabling the adjustment of the axial position of slider block 350 and foot assembly 100 along rail 220 as desired by the surgeon or medical professional.

In this embodiment, complementary segments 362, 364 are configured to permit axial displacement from the lateral segment 357 along the axis 225. In embodiments, body 356 comprises a lipped, grooved, tongue-in-groove, or other interface 366 configured to permit incremental displacement between complementary segments 362, 364 and lateral segment 357. Complementary segments 362, 362 comprise pivots 363, 365 respectively positioned on interface 366 to facilitate incremental displacement. More specifically, complementary segments 362, 364 are configured to laterally displace perpendicular to the axis 225. Complementary segments 362, 364 are configured to incrementally displace laterally, without disengaging second rail 220, by pivoting about pivots 363, 365 respectively and slidably along interface 366. Alternatively, complementary segments 362, 362 may comprise a wedge or cammed surface to incrementally displace from each other. Further, a resilient member configured to facilitate displacement and spacing between complementary segments 362, 364 and lateral segment 357 may be utilized therebetween.

In embodiments, release 368 facilitates the lateral displacement between complementary segments 362, 364. Release 368 is disposed on either complementary segment 362, 364 and comprises a slug 369 disposed in the opposite complementary segment 362, 364. Thus, release 368 allows the surgeon or medical professional to lock the open or closed position thereof, along second rail 220. In this embodiment, release 368 comprises a threaded member or shaft that urges complementary segments 362, 364 (as described hereinabove) into and out of fixed engagement with each other and the rail 220 via a threaded interface within slug 369. In particular, release 368 has a closed position in fixed engagement as described and an unlocked position allowing incremental displacement of complementary segments 362, 364. In this embodiment, the release 368 urged to the closed position, may motivate complementary segments 362, 364 into fixable engagement with the second rail 220. In general, release 368 provides a plurality of contact points within receptor 352, by the translation of complementary segments 362, 364 relative to the lateral segment 357 and each other. In certain instances, the release 368 may be closed such that the complementary segments 362, 364 and lateral segment reversibly retain the pivot arm 140 interface 138 in a fixed position in the retainer 352.

In general, system 10 may be used to support the patient's affected or unaffected leg during a surgery or diagnostic procedure. For use with the patient's affected leg during surgery, the patient's leg is supported by system 10 so as to allow a physician to manipulate the position and angle of the leg to optimize access to a region of interest of the affected leg. In general, system 10 may be attached to the operating table or bed before or after the patient is positioned on the bed. For example, system 10 may be mounted to the bed after the patient is settled, sedated, and/or secured in the bed. To mount system 10 to the bed, first rail 210 is slid onto existing rail 211' of the bed. Quick releases 212 are thereafter extended or clamped such that rail 110 is immovably secured to the bed. System 10 may be fully assembly when rail 210 is secured to the bed, or assembled after securing rail 210 to the bed by coupling second rail 220 to first rail 210 with pivot joint 230, and foot assembly 100 coupled to second rail 220 with block 156.

With system 10 fully assembled and secured to the bed, the foot of the patient's affected leg is secured within boot 110. To facilitate securing the foot in the boot 110, the retainer 134, pivot lock 236, and stop release 158 may be opened or removed from contact such that the pivot 132 and bearing 154 rotate freely and the slider block 150 slides freely along the second rail 220 to enable the maximum degrees of freedom of movement. Alternatively, the interface 138 of the pivot arm 140 may be removed from the retainer 152, by removing the pin 153. In this instance, the system would be temporarily de-coupled while the foot assembly 100 was secured to the patient's foot.

Once the patient's foot is secured in the boot 110, the slider block 150 and the second rail 220 may be positioned as desired, and then locked in place via pivot lock 236 and stop release 158. In particular, pivot lock 236 may be transitioned to the locked position to prevent the swinging of second rail 220 about axis 235, and stop release 158 may be locked such that the slider block 150 is restricted and/or prevented from moving axially along second rail 220. Once a desired position is achieved, the clock foot or shaft 132 may be used to adjust the foot and leg position with respect to the tibial axis T. More specifically, the retainer 134 may be withdrawn to position sole 122 relative to the tibial axis T. The retainer 134 interaction with detent 128 of the boot plate 124 retains the physician's preferred position. Setting or securing the pivot 230 and the slider block 150 from further movement may generally be considered primary adjustments for positioning a leg.

Additionally, bearing 154 is free to rotate about axis C such the angle of between axis D and T may be changed. With stop release 158 in the unlocked position, block 162 and pin 166 are not constraining the rotation of bearing 154. Once the retainer 152 and pivot arm 140 are sufficiently positioned, moving stop release 158 to the locked position causes block 162 and pin 166 to prevent bearing 154 from rotating about axis C. As retainer 152 and pivot arm 140 are coupled thereto, further rotation of these components about axis C is likewise constrained. Setting or securing the position of the shaft 132 and the bearing 154 may generally be considered secondary adjustments for positioning a leg. During surgery, system 10 may be used to periodically reposition the patient's affected leg for optimal access during different stages of the surgery.

The preceding steps may be repeated with the patient's unaffected leg, such that each of the patient's legs are supported by a corresponding system 10. The patient's unaffected leg may generally be positioned such that the surgeon has sufficient access to the affected leg (i.e., such that the surgeon has sufficient space to access the affected leg from many angles or positions). Further, the unaffected leg may be positioned in order to apply or resist fraction forces applied to the affected leg. The unaffected leg is preferably positioned such that the procedure on the affected leg will not injure or cause substantial discomfort, such as stiffness or muscle-strains. As with the patient's affected leg, system 10 may be used to periodically reposition the patient's unaffected leg for optimal access to the affected leg during different stages of the surgery. For diagnostic procedures, system 10 is employed in a similar manner as previously described, except that system 10 is employed to position and hold the patient's leg of interest in one or more desired positions to optimize the diagnostic procedure.

System 10 is configured such that it may be sterilized in whole or in-part. In particular, since system 10 is modular, it may be differentially sterilized dependent on a surgeons preferences and/or the procedure being performed. As is known in the art, sterile drapes are used to cover and isolate unsterilized equipment in an operating room. Components that are covered and below the drape are not necessarily sterilized but, those that are exposed and positioned above the drape must be sterile to reduce the potential for infections. As such, a sterile drape may be positioned such that the entirety of the system 10, including the rail assembly 200 and the boot assembly 100 are exposed, and thus, must be sterilized. Alternatively, only first rail 210 may be covered by the drape with cylindrical element 234 passing upward through a hole in the sterile drape and second rail 220 and boot assembly 100 positioned above the drape. In such cases, first rail 210 may not need to be sterilized, although the other components of system 10 must be sterilized. In further instances, the sterile drape may be configured such that portions of the boot assembly 100 are above the sterile drape, while the remainder of system 10 is below the drape. For example, the drape may fit around the slider block 150, the coupler 153, or the pivot arm 140. In this configuration, both the first rail 210 and the second rail 220 are disposed below the drape, and thus, need not be sterilized, while boot assembly 100 is disposed above the drape, and thus, must be sterilized.

Figure 12:
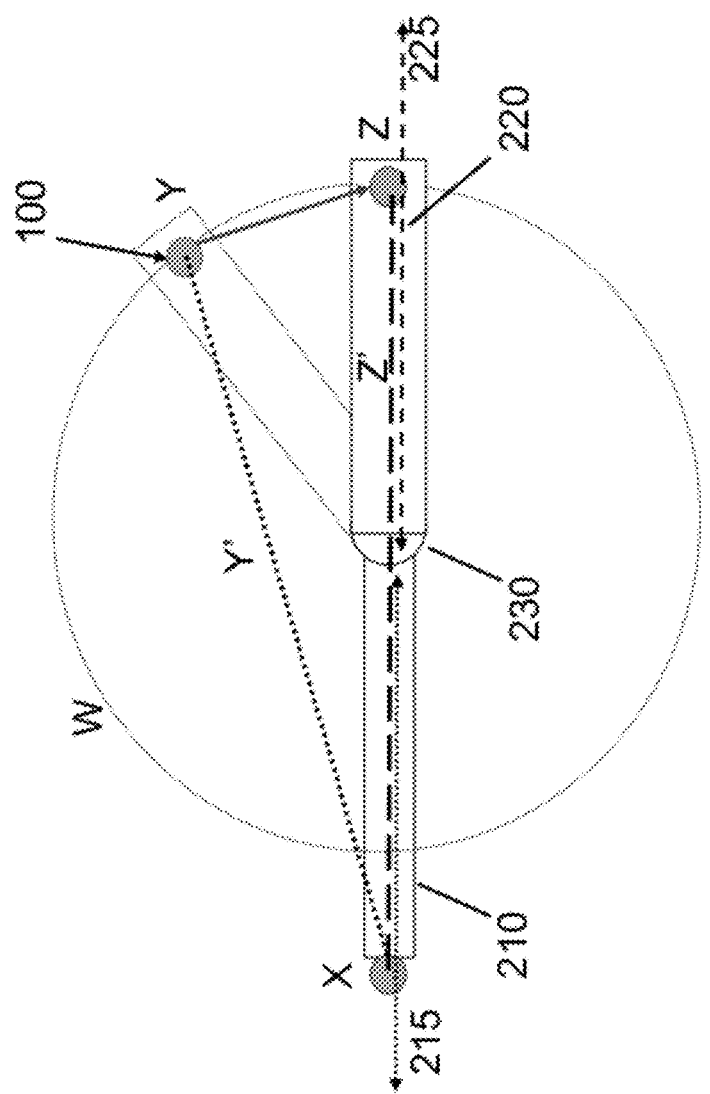
FIG. 12 illustrates a means of applying traction to a patients leg during a procedure.

Referring now to FIG. 12, system 10 can be used to apply fraction to a patient's leg during a procedure by moving boot assembly 100 axially along second rail 220 and/or rotating second rail 220 relative to first rail 210. For example, rotation of second rail 220 about axis 235 defines arc W. The patient's hip or leg joint X is positioned outside arc W, and the patient's foot or ankle is secured to boot assembly 100 at position Y, with second rail 220 rotated laterally relative to first rail 210. Position Y is disposed at a linear distance Y' from the patient's hip or leg joint X. To apply traction, from this position, second rail 220 is rotated medially relative to first rail 210 to move boot assembly 100 along arc W to position Z. Longitudinal axes 215 and 225 of the first rail 210 and the second rail 220 respectively are parallel and in alignment in top view when the boot assembly 100 (fixably positioned on second rail 220) is at position Z on the arc W. At position Z, the linear distance Z' from the patient's leg joint X is greater than the distance Y', thereby applying the tension or traction. It should be appreciated that with this technique for applying fraction, the surgeon does not need to apply tension by pulling or forcing the patient's leg into new positions, but rather uses the pivot 230 as a lever fulcrum to apply the fraction.

Referring again to FIGS. 1 and 2, system 10 is shown as being configured for use with the patient's left leg. However, as previously described, system 10 is reversible, and thus, can be reconfigured for use with the patient's right leg. To re-configure system 10 for right leg support, second rail 220 is removed from the first rail 210 at pivot joint 230—the pivot lock 236 is released such that the cylindrical element 234 may be vertically lifted from the housing 232. Next, the first rail 210 is removed from the patient bed by releasing the quick release connectors 212 and sliding rail 210 axially off of bed rail 211'. The first rail 210 is rotated 180 degrees about axis 215 for positioning on a right side bed rail 211', and then first rail 210 is slid axially along the right side bed rail 211' to the desired position along rail 211' and quick release connectors 212 are tightened to lock first rail 210 to the right side rail 211'. The cylindrical element 234 of the pivot 230 is then inserted into the housing 232 and the pivot lock 236 may be re-tightened as described herein above.

While the forgoing provides an exemplary series of steps for a medical procedure a physician may operate the system 10 in a different sequence. As such the terms primary adjustments and secondary adjustments should not be interpreted as preferred or sequential in meaning. Additionally, the securing or constraining of rotation about all axes of rotation in the system may not be necessary for all procedures.

While preferred embodiments have been shown and described, modifications thereof can be made by one skilled in the art without departing from the scope or teachings herein. The embodiments described herein are exemplary only and are not limiting. Many variations and modifications of the systems, apparatus, and processes described herein are possible and are within the scope of the invention. For example, the relative dimensions of various parts, the materials from which the various parts are made, and other parameters can be varied. Accordingly, the scope of protection is not limited to the embodiments described herein, but is only limited by the claims that follow, the scope of which shall include all equivalents of the subject matter of the claims. Unless expressly stated otherwise, the steps in a method claim may be performed in any order. The recitation of identifiers such as (a), (b), (c) or (1), (2), (3) before steps in a method claim are not intended to and do not specify a particular order to the steps, but rather are used to simplify subsequent reference to such steps.

The invention claimed is:

1. A system comprising:
   a rail assembly having a first rail pivotally coupled to a second rail, each rail having a longitudinal axis;
   a slider block slidably mounted to the second rail;

a pivot arm pivotally coupled to the slider block, wherein the pivot arm is configured to rotate about a vertical axis and a horizontal axis relative to the slider block, wherein the horizontal axis intersects the vertical axis;

a sole assembly coupled to the pivot arm with a rotatable coupling configured to allow the sole assembly to rotate about a tibial axis relative to the pivot arm, wherein the vertical axis intersects the tibial axis; and a boot mounted to the sole assembly, wherein the boot is configured to receive a patient's foot and align the patient's tibia with the tibial axis;

wherein the rotatable coupling includes an incremental locking mechanism including a locked position and an unlocked position;

wherein, when the incremental locking mechanism is in the locked position, the incremental locking mechanism is configured to releasably lock the rotational position of the sole assembly about the tibial axis independent of the rotational position of the pivot arm about the vertical axis and independent of the rotational position of the pivot arm about horizontal axis;

wherein, when the incremental locking mechanism is in the unlocked position, the incremental locking mechanism is configured to allow rotation of the sole assembly relative to the incremental locking mechanism only about the tibial axis.

2. The system of claim 1, wherein the first rail comprises a quick release configured to releasably lock the first rail to a mating rail of a patient's bed or operating table.

3. The system of claim 1, wherein the first rail and the second rail are pivotally coupled end-to-end.

4. The system of claim 3, wherein the first rail has a first end and a second end opposite the first end, wherein the first end of the first rail is configured to releasably couple the device to a bed for a patient;

wherein the second rail has a first end and a second end opposite the first end, wherein the first rail and the second rail are oriented horizontally;

a pivot joint rotatably coupling the second end of the first rail to the first end of the second rail, wherein the pivot joint is configured to allow the second rail to rotate relative to the first rail about a vertical axis of rotation;

wherein the pivot joint is configured to be positioned at a first distance from a hip joint of the patient that is greater than a second distance from the pivot joint to the second end of the second rail.

5. The system of claim 1, wherein an end of the first rail is rotatably coupled to an end of the second rail with a pivot joint configured to allow the second rail to rotate relative to the first rail about the end of the second rail.

6. The system of claim 5, wherein the pivot joint comprises a tubular housing disposed at the end of the first rail and a cylindrical member disposed at the end of the second rail;

wherein the cylindrical member is coaxially disposed within the housing and slidingly engages the housing;

wherein the pivot joint has an vertical axis of rotation.

7. The system of claim 6, wherein the longitudinal axis of each rail is oriented perpendicular to the axis of rotation.

8. The system of claim 5, wherein the longitudinal axis of the second rail is configured to rotate in a plane that is parallel to the longitudinal axis of the first rail.

9. The system of claim 1, further comprising an annular bearing rotatably coupled to the slider block, wherein the annular bearing is configured to rotate about the vertical axis relative to the slider block.

10. The system of claim 9, wherein the pivot arm is pivotally coupled to the annular bearing.

11. The system of claim 10, wherein the pivot arm is coupled to the annular bearing with a pin defining the horizontal axis.

12. The system of claim 11, wherein the pivot arm comprises a stop configured to limit the angle of rotation of the pivot arm about the horizontal axis.

13. The system of claim 1, wherein the slider block comprises a first locking mechanism configured to releasably lock the axial position of the slider block along the second rail.

14. The system of claim 13, wherein the slider block comprises a second locking mechanism configured to releasably lock the rotational position of the pivot arm relative to the slider block.

15. The system of claim 1, wherein the sole assembly comprises a planar boot sole coupled to the boot.

16. The system of claim 15, wherein the planar boot sole is rotatably coupled to the pivot arm with the rotatable coupling.

17. The system of claim 16, wherein the incremental locking mechanism is configured to releasably lock the rotational position of the planar boot sole about the tibial axis relative to the pivot arm.

18. A device for supporting a leg of a patient, comprising:

a first rail having a longitudinal axis, a first end, and a second end opposite the first end, wherein the first end of the first rail is configured to releasably couple the device to a bed for a patient;

a second rail having a longitudinal axis, a first end, and a second end opposite the first end, wherein the first rail and the second rail are oriented horizontally;

a pivot joint rotatably coupling the second end of the first rail to the first end of the second rail, wherein the pivot joint is configured to allow the second rail to rotate relative to the first rail only about a vertical axis of rotation;

wherein the pivot joint is configured to be positioned at a first distance from a hip joint of the patient that is greater than a second distance from the pivot joint to the second end of the second rail;

a slider block moveably mounted to the second rail; and a foot holder configured to hold a foot of the patient coupled to the slider block.

19. The device of claim 18, wherein the foot holder is pivotally coupled to the slider block.

20. The device of claim 19, wherein the foot holder is configured to be rotated a first axis of rotation, a second axis of rotation, and a third axis of rotation relative to the slider block.

21. The device of claim 18, wherein the slider block includes a locking mechanism configured to releasably lock the axial position of the slider block along the second rail.

22. The device of claim 21, wherein the first rail includes a locking mechanism configured to lock the axial position of the first rail along a mating rail of a bed or table.

23. The system of claim 1, wherein the rotatable coupling is configured to releasably lock the rotational position of the sole assembly about the tibial axis at predetermined angular positions angularly spaced about 2-5° apart.

* * * * *